(12) United States Patent
Jetty et al.

(10) Patent No.: US 6,838,268 B2
(45) Date of Patent: Jan. 4, 2005

(54) PROCESS FOR THE PREPARATION OF β-KETO ALIPHATIC ACID ESTER

(75) Inventors: Annapurna Jetty, Andhra Pradesh (IN); Dattatray M. Akkewar, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/625,519

(22) Filed: Jul. 24, 2003

(65) Prior Publication Data

US 2004/0053380 A1 Mar. 18, 2004

Related U.S. Application Data

(62) Division of application No. 10/098,505, filed on Mar. 18, 2002.

(51) Int. Cl.$^7$ ............... C12P 7/62; A61K 31/235; A61K 35/00
(52) U.S. Cl. ............... 435/135; 424/115; 514/545
(58) Field of Search ............... 435/135; 424/115; 514/545

(56) References Cited

U.S. PATENT DOCUMENTS 5,229,279 A    7/1993   Peoples et al.

*Primary Examiner*—Herbert J. Lilling
(74) *Attorney, Agent, or Firm*—Burns, Doane, Swecker & Mathis, L.L.P.

(57) ABSTRACT

The present invention provides a process for the preparation of antimicrobial compound β-keto aliphatic acid ester, a novel, aliphatic, fatty acid derivative from *Bacillus* sp. IICT-001.

8 Claims, No Drawings

PROCESS FOR THE PREPARATION OF β-KETO ALIPHATIC ACID ESTER

This application is a divisional of application Ser. No. 10/098,505, filed on Mar. 18, 2002.

FIELD OF THE INVENTION

The present invention relates to a process for preparation of β-keto aliphatic acid ester. The present invention particularly relates to a process for the preparation of antimicrobial compound β-keto aliphatic acid ester, a novel, aliphatic, fatty acid derivative from Bacillus sp. IICT-001.

BACKGROUND OF THE INVENTION

Fatty acid derivatives, which are mainly of fungal and bacterial metabolites, are subdivided into saturated and unsaturated type of compounds. A number of compounds have been isolated from Bacillus sp. in the art, such as iso-13 methyl tetradecanoic acid, fatty acid (Arch. Vetr. Ital 20,215 1969) peptide (Shoji et al., J. Antibiotics activity (Aszalos et al, J. Chromatography, 37, 477, 1968). The antibacterial pseudomonic acid produced by a Pseudomonas species represents an interesting new type of fatty acid ester (Berdy, CRC Hand Book of Antibiotic Compounds Vol VI p-391 1980). It contains several unusual chemical features in this family, such as epoxy, pyran and 9-hydroxy nonanic acid constituents. These compounds are normally soluble in nonpolar organic solvents such as hydrocarbons. Hydroxy acid was isolated primarily from bacterial species (Berdy, CRC Hand Book of Antibiotic Compound Vol II, 35, 1980). Antimicrobial and antitumor activity of natural fatty acids derived from different kinds of microbes including fungi Actinomycetes or Myxobacteria, is a frequently reported property of such type of compounds. Fatty acid esters (Glycerides) such as monoolein, monolaurin, eoixenotid, pseudomonic acid $A_f$-B were isolated from different microbes with varied antimicrobial activity.

Cyclic acylpeptide, halobacillin from Bacillus species 11-cycloheptyl-2hydroxy undecanoic acid from thermo acidic Bacillus sp, sarcinic acid from different Bacillus sp. have been reported by earlier workers (Comprehensive natural products chemistry Vol 8 1986).

OBJECTS OF THE INVENTION

The main object of the present invention is to provide a process for the preparation of β-keto aliphatic avid ester, useful as therapeutic agent, a novel aliphatic acid ester from Bacillus species IICT-001 to isolate novel antimicrobial compounds from microbes, by screening many organisms from different soil samples and isolated a new strain designated as IICT-001 to produce potent antimicrobial compounds.

Another object of the present invention is the isolation, separation, purification and practical structure elucidation of a new bioactive, aliphatic, β-keto acid ester for the first time from a new strain of Bacillus sp. IICT 001.

Still another object of the present invention is that the new source for a new antimicrobial compound β-keto aliphatic acid ester, showing very good broad spectrum antimicrobial activity may be used as a new antibiotic with simple isolation process and might result in a new potent source of pharmaceutically active drug.

SUMMARY OF THE INVENTION

Accordingly, the present invention provides a process for preparation of β-keto aliphatic acid ester which comprises: growing a Bacillus sp. IICT 001 in growth medium for a period of at least 3–4 days to obtain broth, extracting the said broth with organic solvent, removing the solvent and purifying the β-keto aliphatic acid ester compound.

In an embodiment of the invention the growth medium used is selected from the group consisting of nutrient medium and mineral salts medium.

In another embodiment of the invention the growth medium is supplemented with protein and carbon content such as soyabean meal, corn steep liquor, casein, casein hydrolysate glucose, malt extract.

In yet another embodiment of the invention, the growth of strain is carried out at a temperature range of 20 to 40° C. and a pH in the range of 4.5–7.5.

In another embodiment of the invention the solvents for extraction of broth used comprises a chlorinated organic solvent selected from the group consisting of chloroform, dichloromethane, dichloroethane, and ethyl acetate; or a polar solvent selected from the group consisting of methanol, ethanol and a mixture thereof.

In yet another embodiment of the invention the chromatographic method used comprises thin layer chromatography using silica gel as stationary phase and 1:1 methanol $CHCl_3$ as mobile phase.

DETAILED DESCRIPTION OF THE INVENTION

The present invention relates to a process for the preparation of β-keto aliphatic acid ester, a novel aliphatic β-keto acid ester from Bacillus sp. IICT-001 a strain to produce potent antimicrobial compound, isolated in our pursuit to identify novel antimicrobial compound from terrestrial soil sample of Hyderabad. The new strain is identified based on microscopic, morphological, physiological and biochemical characteristics described in tables as Bacillus sp., which was grown in soyameal supplemented broth at optimum pH and temperature and extracting the said bacterial culture broth with non-polar solvents such as chloroform and ethyl acetate in combination with methanol, ethanol to extract through the antimicrobial compound in a known manner to get a crude fraction and purifying the antibiotic from the said crude fraction by conventional chromatography to recover antibiotic β-keto aliphatic acid ester.

The new strain IICT-001 is easy to grow and maintain, and multiplies profusely on nutrient broth The production of antibiotic is good in a conventional soyabean meal supplemented production medium constituting soyabean meal 10 g, glucose 10 g, sodium chloride 5 g, calcium carbonate 1 g, water 1 lt. at optimum pH and optimum temperature.

The present strain Bacillus species is a gram positive, moving rods with bulging sporangia. The temperature range for the growth is 20–45° C. and the pH range is 4.5–8.0. The sodium chloride tolerance is recorded to be 4.0–7.0% Table 1 shows the colony characters while Table 2 shows the physiological characteristics such as temperature, pH, and sodium chloride tolerance. Tables 3 and 4 show the biochemical properties and utilisation of carbon source for the strain respectively.

TABLE 1

| | |
|---|---|
| Margin | Smooth |
| Elevations | − |
| Pigments | − |
| Grams reactions | + |

TABLE 1-continued

| | |
|---|---|
| Shape | Rods |
| Size | Small celled |
| Endospore | + |
| Position of spore | C |
| Sporangia bulging | + |
| Motility | + |

TABLE 2

Physiological characteristics of strain Bacillus sp IICT 001

| | | |
|---|---|---|
| 1 | Temperature range for growth | 20–45° C. |
| 2 | Optimum temperature for antibiotic protection | 20–40° C. |
| 3 | PH range for the growth | 4.5–9.0° C. |
| 4 | Optimum pH for antibiotic protection | 6–9° C. |
| 5 | Sodium chloride tolerance | 2.5–8.0° C. |

TABLE 3

Biochemical characteristics of strain Bacillus sp

| | | |
|---|---|---|
| 1 | Citrate utilisation | Negative |
| 2 | Caesin hydrolysis | Positive |
| 3 | Starch hydrolysis | Positive |
| 4 | Urea hydrolysis | Negative |
| S | H$_2$S production | Negative |
| 6 | Catalase | Positive |

TABLE 4

Utilisation of carbon sources and acid production by strain Bacillus sp. IICT 001

| | |
|---|---|
| Arabinose | Negative |
| Cellobiose | Positive |
| Dextrose | Positive |
| Fructose | Positive |
| Galactose | Negative |
| Lactose | Negative |
| Maltose | Positive |
| Sucrose | Positive |

Based on the above properties the strain IICT-001 is identified as *Bacillus* sp. It differs from the type *Bacillus* sp. in the following properties. Optimum pH is 5.5–8.0, optimum temperature is 30–45° C., there is no growth conditions, The present strain *Bacillus* sp 001 differs from known *Bacillus* sp, in that it produces novel antibiotic under optimum temperature, pH and growth conditions, The growth conditions are requirement of carbon and nitrogen source along with macro and micronutrients for optimum yield of antimicrobial compound.(Buchanan and Gibbons, Bergy's Manual of Determinative Bacteriology, 8th ED., P.540, 1974; Sonenshein et al, *Bacillus* sp. American society for Microbiol, Washington D.C.P.13, 1993).

The bioassay guided isolation and purification has resulted in yellow viscous, UV positive compound soluble in organic solvents identified as β-keto aliphatic acid ester based on its physical and spectral properties. The spectral properties are as follows.
UV max (MeOH):225
$^1$H NMR CDCl$_3$(80 M$\underline{H}_2$): 0.88 t (C$\underline{H}_3$); 1.25 s, br (C$\underline{H}_2$)n; 2.16s(COC$\underline{H}_2$);
3.68 s(COOC$\underline{H}_3$)IR, $^\nu$max(CHCI$^3$): cm$^{-1,}$ 1730 (ester), 1670 (Carbonyl).

This organism is very stable and the compound production is continuous without loss of activity. The compound produced is also stable at around 80° C. also.

The present invention provides a process for preparation of β-keto aliphatic acid ester, by growing a novel strain *Bacillus* sp. in production medium for a period of at least 3–4 days in a conventional manner to obtain broth, extracting the said broth with organic solvent, removing the solvent and purifying the acid ester compound by conventional chromatographic methods, The growth medium used may be such as nutrient medium and mineral salts medium. The medium may be supplemented with protein and carbon content such as soyabean meal, corn steep liquor, caesin, caesin hydrolysate glucose, malt extract. Growth of strain may be carried out at a temperature range of 20 C. to 40 C. and pH in the range of 4.5–7.5. The solvents for extraction of broth used may be chlorinated organic solvents such as chloroform, dichloromethane, dichloroethane, and ethyl acetate, polar solvents such as methanol, ethanol and mixture thereof.

The chromatographic method used may be such as thin layer chromatography using silica gel as stationary phase and 1:1 methanol:CHCl$_3$ as mobile phase. The active band is eluted with the same solvent.

The process for the preparation of β-keto aliphatic acid ester, a novel aliphatic β-keto acid ester from *Bacillus* sp. IICT-001 a stain to produce potent antimicrobial compound, isolated in our pursuit to identify novel antimicrobial compound from terrestrial soil sample of Hyderabad. The new strain is identified based on microscopic, morphological, physiological and biochemical characteristics described in tables as *Bacillus* sp., which was grown in soyameal supplemented broth at optimum pH and temperature and extracting the said bacterial culture broth with non-polar solvents such as chloroform and ethyl acetate in combination with methanol, ethanol to extract through the antimicrobial compound in a known manner to get a crude fraction and purifying the antibiotic from the said crude fraction by conventional chromatography to recover antibiotic β-keto aliphatic acid ester.

The following examples are given by way of illustration of the present invention and therefore should not be construed to limit the scope of the present invention.

EXAMPLE 1

4 day old culture broth (2 lt) of *Bacillus* sp. is prepared with Soya supplemented medium constituting soya bean meal 20 g, glucose 20 g, sodium chloride 10 g, CaCo$_3$ 2 g, water 2 l at optimum pH and optimum temperature and sterilized at 15 pounds pressure for 20 mts. After it is cooled to room temperature a 10% inoculum grown for 24 hr. in the same culture medium is transferred aseptically to the above production medium and kept on shaker at 150 RPM for 4 days at 28+2° C. is extracted thoroughly with 1.5 l of ethyl acetate. The active organic crude extract (572) mg is used for further purification. The active compound purified by TLC using silica gel and 10% MeOH in CHCl$_3$ as mobile phase and the active UV positive band having an RF value of 0.6400 is eluted with the same solvent to get an yellow viscous antimicrobial compound (Yield 23.7 mg) of formula 1,

EXAMPLE 2

5 day old culture broth (3 lt) of *Bacillus* sp grown in soya amended broth grown on orbital shaker at 37° C. at 170 RPM is extracted thoroughly with 20% MeOH in CHCl$_3$. The organic extracts pooled evaporated under vacuum at 40° C. to get 853 mg of crude fraction, which is purified by chromatography using a mixture of MeOH:CHCl$_3$ and eluted with the same solvent system to get pure, active yellow viscous antimicrobial compound (yield 35.12 mg) of formula 1.

EXAMPLE 3

6 day old culture broth (4 lt) of *Bacillus* sp. grown in soya amended medium at 35° C. at 170 RPM is extracted thoroughly with 5% $CHCl_3$:MeOH. The organic extracts pooled evaporated under vacuum at 37° C. to get 1.12 gm of crude fraction, which is purified by chromatography using silica gel as stationary phase and 10% methanol in chloroform as mobile phase. The active band is eluted with the same solvent to get pure, antibacterial, yellow viscous compound (yield 46.89 mg) of formula 1.

EXAMPLE 4

3 days old culture broth (1 lt) of *Bacillus* sp. grown in amended medium at 30° C. at 160 RPM is extracted thoroughly with chloroform in combination with methanol. The organic extracts pooled, evaporated under vacuum at. 36° C. to get 284 mg of crude fraction, which is purified by chromatography using silica gel as stationary phase and 5% methanol in chloroform as mobile phase. The active band is eluted with the same solvent to get pure, antibacterial, yellow viscous compound (yield 11.71 mg) of formula 1.

EXAMPLE 5

7 day old culture broth (2.5 lt) of *Bacillus* sp. grown in soya amended medium at 32° C. at 150 RPM is extracted thoroughly with dichloromethane in combination with methanol. The organic extracts pooled, evaporated under vacuum at 36° C. to get 709 mg of crude fraction, which is purified by chromatography using silica gel as stationary phase and 5% methanol in chloroform as mobile phase. The active band is eluted with same solvent to get pure, antibacterial yellow viscous compound (yield 16.98 mg) of formula 1.

Anti Microbial Assay:

All the media used are from Hi Media, Bombay, India Bacterial strains were grown on nutrient agar and suspended in Muller Hinton broth and fungal strains in sabouroud broth A conventional two fold serial dilution method is employed to determine minimum inhibitory concentration (Jones et al, 1984;In: Lenette EH, Ballows et al., Manual of clinical Microbiol., 972–977, Washington D.C., American Society for Microbiol). The compound dissolved in acetone at 2. mg/ml concentration is diluted in respective broths in the range of 100–1.56 µg/ml culture grown at 37° C. for 20 h were used as inoculum (approximately $10^{5-6}$ CFU/ml). Test cultures were incubated at 37° C. for 24 h. All the results (average of triplicates) were presented in µg/ml (Table 5). The lowest concentration of antimicrobial agent that results in the complete inhibition of microorganism represents the minimum inhibitory concentration (MIC (µg/ml).

The activity against the following organisms have been tested and the minimum inhibitory concentration against test microbes is presented in Table 5.

TABLE 5

Antimicrobial activity of β-keto aliphatic acid ester from Bacillus sp. IICT 001

| No. | microorganism | Concentration of compound µg/ml |
|---|---|---|
| 1 | Arthrobacter citrius | <50 |
| 2 | Bacillus cereus | <6.25 |
| 3 | B. licheniformis | <25 |
| 4 | B. polymixa | <12.5 |
| 5 | B. pumilus | <12.5 |
| 6 | B. subtilis | <25 |
| 7 | Closiridium sp. | <25 |
| 8 | Staphylococcus aureus | <12.5 |
| 9 | Streptococcus sp. | <25 |
| 10 | Escherichia coli | <3.12 |
| 11 | Kiebsiella aerogenes | <12.5 |
| 12 | Pseudomonas aureoginosa | <6.25 |
| 13 | P. putida | <12.5 |
| 14 | Salmonella typhimurium | <6.25 |
| 15 | Sarcina lutea | <12.5 |
| 16 | Nocardia sp. | <25 |
| 17 | Candida albicans | <12.5 |
| 18 | Saccharomyces cerevisiae | <50 |

The Main Advantages of the Present Invention are:

1. The maintenance of the organism is easy and growth is good in variety of nutrient media.
3. The antimicrobial compound is isolatable at varied temperatures (20–40° C.).
4. The antimicrobial compound is active on variety of microorganisms such as gram positive and gram negative bacteria and fungi.
5. The compound is active at low concentration on many organisms.
6. The organism is very stable and activity is reproducible for many generations tested for years.
7. The culture *Bacillus* sp. IICT 001 can be stored in refrigerator safely without any loss of activity.

We claim:

1. A process for preparation of B-keto aliphatic acid ester, which comprises growing a *Bacillus* sp. IICT 001 in growth medium for a period of at least 3–4 days to obtain broth, extracting the said broth with organic solvent, removing the solvent and purifying the β-keto aliphatic acid ester.

2. A process as claimed in claim 1 wherein the growth medium used is selected from the group consisting of nutrient medium and mineral salts medium.

3. A process as claimed in claim 1 wherein the growth medium is supplemented with protein and carbon content selected from the group consisting of soyabean meal, corn steep liquor, casein, casein hydrolysate glucose and malt extract.

4. A process as claimed in claim 1 wherein the growth of strain is carried out at a temperature range of 20 to 40° C. and a pH in the range of 4.5–7.5.

5. A process as claimed in claim 1 wherein the solvent for extraction of broth is a chlorinated organic solvent selected from the group consisting of chloroform, dichloromethane and dichloroethane.

6. A process as claimed in claim 1 wherein the solvent for extraction of broth is ethyl acetate.

7. A process as claimed in claim 1 wherein the solvent for extraction of broth is a polar solvent selected from the group consisting of methanol, ethanol and a mixture thereof.

8. A process as claimed in claim 1 wherein the chromatographic method used comprises thin layer chromatography using silica gel as stationary phase and 1:1 methanol $CHCl^3$ as mobile phase, column chromatography, high pressure liquid chromatography.

* * * * *